US008738548B2

(12) United States Patent
Parvin et al.

(10) Patent No.: US 8,738,548 B2
(45) Date of Patent: May 27, 2014

(54) SYSTEM AND METHOD FOR DETERMINING AN OPTIMUM QC STRATEGY FOR IMMEDIATE RELEASE RESULTS

(75) Inventors: Curtis Alan Parvin, McKinney, TX (US); John C. Yundt-Pacheco, Fairview, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 228 days.

(21) Appl. No.: 13/167,472

(22) Filed: Jun. 23, 2011

(65) Prior Publication Data

US 2012/0330866 A1  Dec. 27, 2012

(51) Int. Cl.
 *G01N 37/00* (2006.01)
 *G06F 15/18* (2006.01)
 *G06N 99/00* (2010.01)

(52) U.S. Cl.
 CPC .................................... *G06N 99/005* (2013.01)
 USPC .................................. 706/12; 706/47; 702/81

(58) Field of Classification Search
 None
 See application file for complete search history.

(56) References Cited

U.S. PATENT DOCUMENTS

| 5,937,364 | A | 8/1999 | Westgard et al. | |
|---|---|---|---|---|
| 7,050,933 | B2 | 5/2006 | Parvin et al. | |
| 2003/0101012 | A1* | 5/2003 | Parvin et al. | 702/84 |
| 2010/0145630 | A1 | 6/2010 | Ball et al. | |
| 2010/0295685 | A1* | 11/2010 | Parvin et al. | 340/573.1 |

OTHER PUBLICATIONS

Westgard, James, O., et al., "Design and Evaluation of Statistical Control Procedures: Applications of a Computer 'Quality Control Simulator' Program," Clinical Chemistry, 1981, vol. 27, No. 9, pp. 1536-1545.
Dechert, Jerry, et al., "Multivariate approach to quality control in clinical chemistry," Clinical Chemistry, 1998, vol. 44, No. 9, pp. 1959-1963.
International Search Report and Written Opinion mailed Sep. 18, 2012, PCT/US12/43582, 8 pages.
Parvin, Curtis, A., "Assessing the Impact of the Frequency of Quality Control Testing on the Quality of Reported Patient Results," Clinical Chemistry, 2008, vol. 54, No. 12, pp. 2049-2054.
Parvin, Curtis, A., "New Insight into the Comparative Power of Quality-Control Rules that Use Control Observations within a Single Analytical Run," Clinical Chemistry, 1993, vol. 39, No. 3, pp. 440-447.

* cited by examiner

*Primary Examiner* — Alan Chen
(74) *Attorney, Agent, or Firm* — Kilpatrick Townsend & Stockton LLP

(57) ABSTRACT

The present invention proposes a method for optimizing a quality control strategy for rapid release results. An embodiment of the invention includes generating a set of candidate quality control rules and for each candidate rule, computing a maximum number of patient specimens that can be tested between quality control events while keeping the expected number of correctable unacceptable results below a predetermined correctable maximum and keeping the expected number of final unacceptable results below a predetermined final maximum. Furthermore a quality control utilization rate can be computed based on the number of patient specimens tested between each quality control event and the number of reference samples tested at each quality control event. The candidate rule for which the best quality control utilization rate may be selected along with the corresponding number of patients to be tested between each quality control as the optimum quality control strategy.

26 Claims, 9 Drawing Sheets

| Reference Value | Actual Result |
|---|---|
| 100 | 102 |
| 100 | 103 |
| 150 | 146 |
| 150 | 153 |
| 200 | 192 |
| 200 | 201 |

FIG. 8

| Reference Value $(E_i)$ | SD $(\sigma_i)$ | Actual Result $(O_i)$ | Difference $(O_i - E_i)$ | Difference divided by SD $\left(\dfrac{O_i - E_i}{\sigma_i}\right)$ | (Difference divided by SD)$^2$ $\left(\dfrac{O_i - E_i}{\sigma_i}\right)^2$ |
|---|---|---|---|---|---|
| 100 | 3 | 102 | 2 | 0.67 | 0.444 |
| 100 | 3 | 103 | 3 | 1 | 1.000 |
| 150 | 3.5 | 146 | -4 | -1.14 | 1.306 |
| 150 | 3.5 | 153 | 3 | 0.86 | 0.735 |
| 200 | 4 | 192 | -8 | -2 | 4.000 |
| 200 | 4 | 201 | 1 | 0.25 | 0.063 |
|  |  |  |  | Sum $(\chi^2)$: | 7.548 |

FIG. 9

SYSTEM AND METHOD FOR DETERMINING AN OPTIMUM QC STRATEGY FOR IMMEDIATE RELEASE RESULTS

BACKGROUND

Diagnostic devices are used for a number of purposes in medicine, research and other industries. For example in medicine, a device may be used to measure the concentration of a particular substance in a blood or urine sample. In all such applications it is important to ensure that the diagnostic device operates properly and that the results returned are correct. In particular it is important to ensure that the device is not operating with a systematic error that can corrupt a large portion of results produced.

When a sample is tested, the equipment will return a test result, which may differ from the correct value. A result may be deemed to be acceptable if the difference between the reported result and the actual result is within a predetermined range or margin of error. Since there often is no way to know the correct value of the samples submitted for testing, the equipment may be periodically tested to detect incorrectly reported results and systematic errors.

In order to test the equipment, an operator may test one or more reference samples for which the correct result is known. Where a patient sample may only be stable for a number of hours or days after collection, a reference sample may be a synthetic sample designed to be stable and testable for a much longer period of time, such as a number of months or years. Once the testing values for the reference samples are obtained they may be verified against a set of predetermined Quality Control ("QC") criteria. Conducting this procedure, whether one or more samples are tested, may be referred to as a QC event. When more than one sample is tested, one sample with a corresponding normal value, one with an abnormally high value and one with an abnormally low may be tested to ensure that equipment returns correct results across the entire scale of results. Furthermore, a number of samples with the same value may be tested to ensure that the equipment consistently returns the same results.

If the results meet the QC criteria, the equipment is determined to be returning good results and accordingly not subject to any systematic errors, and it can be used to test further patient samples. If the results do not meet the prescribed criteria, the equipment is likely to have started malfunctioning at some point before or during the QC event. The malfunctioning may have started after testing the last patient sample, but before the QC event, in which case all the patient results will have been reported correctly. On the converse the error can have occurred at any point in time before the QC event, and all the results reported for the patient samples tested following such failure may have been reported with an error greater than the acceptable margin of error.

If patient results obtained after a successful QC event are not released until the following QC event has been passed, the number of reported errors can be greatly reduced. The need for immediate release of test results often renders this option impractical, and another solution is therefore needed.

The operator can in general decrease the expected number of erroneously reported patient results by increasing the number of QC events and by testing more reference samples at each QC event. However, increasing either of these increases cost and decreases the number of patient samples that can be tested by the equipment during any period of time.

BRIEF SUMMARY

The present invention proposes a method for optimizing a quality control strategy for immediate release results. An embodiment of the invention includes generating a set of candidate quality control rules and for each candidate rule, computing a maximum number of patient specimens that can be tested between quality control events while keeping the expected number of unacceptable results below a prespecified maximum. Furthermore a quality control utilization rate can be computed based on the number of patient specimens tested between each quality control event and the number of reference samples tested at each quality control event. The candidate rule with the best quality control utilization rate may be selected as the optimum quality control strategy.

BRIEF DESCRIPTION OF THE DRAWINGS

FIG. 4 shows how the expected number of errors varies with the size of a systematic error that the system is subjected to;

FIG. 8 shows a table of reference values and test values for samples tested during a QC event.

FIG. 9 shows a table of calculations used in relation to the chi-squared test for the QC event test values shown in FIG. 8.

DETAILED DESCRIPTION

When implementing a quality control (QC) strategy to obtain particular performance targets for immediate release results it is difficult to determine a strategy that uses the minimal number of quality control tests while still obtaining the desired performance targets. In particular, when merely increasing the frequency of QC events and the number of samples tested at each QC event the resulting QC strategy may require an excessive number of tests of reference-samples to achieve the desired QC goals. Certain embodiments of the present invention may be used to determine an optimal QC strategy that meets requirements for an expected number of correctable and final unacceptable results.

I. Overview

Figure 1:
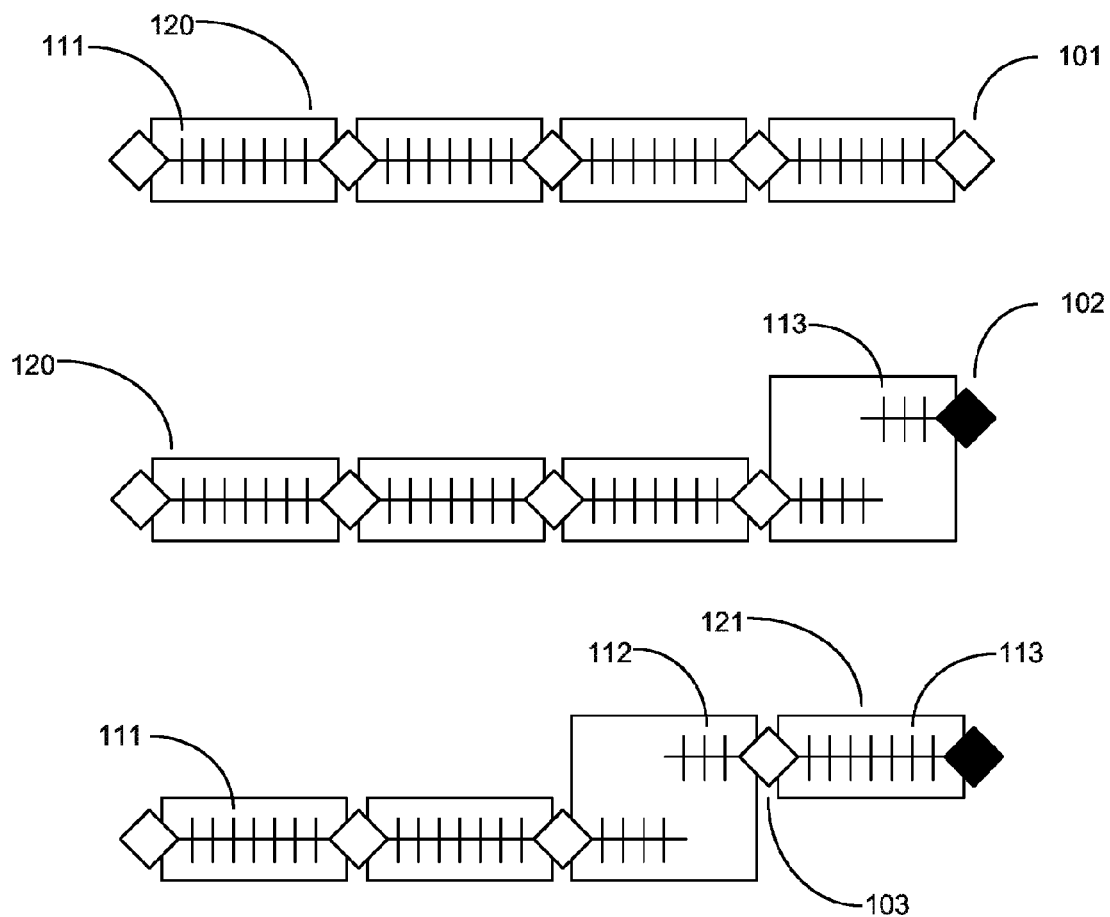
FIG. 1 shows three different scenarios of diagnostic testing where each scenario includes four QC-intervals and five QC-events.

FIG. 1 shows three potential sequences of test-results from diagnostic tests. The first row shows four sets of test-results or QC-intervals (120) where all the results are produced with no systematic error present. The time when each patient test result was obtained is indicated with a vertical line (111). A passed QC-event (101) is shown before and after each QC-interval. The second row shows four QC-intervals where a systematic error occurred in the fourth QC-interval. Affected results (113) are shifted relative to unaffected results. The failed QC-event following the systematic error (102) is shown in black. Since the affected results occurred after the last passed QC-event they are correctable. The third row shows four sets of QC-intervals, where a systematic error occurred in the third QC-interval. The QC-event following the systematic error was passed. Patient results with final errors (112) are those affected results that occurred before the passed QC event, correctable errors (113) are those that occurred after the last passed QC-event (103).

It is in the interest of any operator of diagnostic equipment to limit both the number of correctable and final errors. However, when there is a fixed amount of resources made available for quality control, the measures used to reduce the number of correctable errors may adversely affect the number of final errors and vice-versa. For example, if more reference samples are tested at each QC event, more patient samples must be tested between each QC event. While this shift may reduce the chance of a final error, it may increase the expected number of correctable errors after a QC failure. An approach for finding an appropriate balance is therefore needed.

II. Performance Targets

In an embodiment, good lab practice dictates that upon a QC failure, the operator will investigate the patient samples that were tested between the previously passed QC event and the failed QC event. The erroneous results reported during this time may be referred to as correctable as the lab may retest these samples and inform patients of the new, correct results. If erroneous results were reported prior to the last QC pass, these results may be referred to as final because the erroneous results will be the final report from the lab.

In another embodiment, practice is to retest a lower number of samples. For example, if a lab tests 100 samples between each QC event, it may decide to only retest the last 50 samples following a QC event. In this case the erroneous results among those last 50 will be correctable errors, and any error in earlier samples will be final.

In yet another embodiment of the invention, practice is to retest a greater number of samples. A lab testing 100 samples between each QC event may decide to retest the last 200 samples on a QC failure. Similarly, any erroneous result among the last 200 samples will be correctable, and any erroneous result prior to these will be final.

This window of retesting may be expressed as a factor of the number of samples tested between each QC event. For example, if 200 samples are tested and there are 100 samples between each QC event, this factor would be 2. Where not otherwise stated, this factor of retesting will be assumed to be 1 as shown in FIG. 1.

When the factor of retesting is constant, the number of correctable errors can be controlled by increasing or decreasing the number of patient samples between QC events. For example, if a QC event is conducted between every 20 samples, there will be no more than 20 correctable mistakes following a QC failure.

In another embodiment of the invention this can be specified as an absolute maximum per systematic error. For example, it can be specified that in the event of a systematic error, there should be a maximum of 10 final errors and 50 correctable errors. In yet another embodiment of the invention this can be specified in terms of the expected number of errors. For example, it may be specified that in the event of a systematic error, the expected number of final errors should be no more than 5 and the expected number of correctable errors should be no more than 10.

The QC utilization rate of a particular strategy may be expressed as the average number of reference samples tested at each QC event divided by the average number of patient samples tested between QC events. For example if 100 patient samples are tested between QC events and 6 reference samples are tested during each QC event then the QC utilization rate is 6/100=0.06=6%. This metric may be measured in a number of different ways.

In an embodiment of the invention a quality control strategy is selected such that it minimizes the QC utilization rate while meeting the performance targets.

In addition to the performance targets, the optimization may in an embodiment of the invention rely of certain properties of the diagnostic equipment, including a system stability factor ($P_F$) and a sigma metric ($\sigma_M$) of the system.

In one embodiment of the invention the system stability factor ($P_F$) indicates the portion of system failures that result in a systematic error at least as large as the quality specification for the analyte. For example, an unstable system may have a $P_F=0.5$, a moderately stable system $P_F=0.25$, and a stable system $P_F=0.1$. In this case, for the stable system, only 10% of system failures will result in a systematic error as large or larger than the quality specification of the analyte.

In an embodiment of the invention the sigma metric of the test system ($\sigma_M$) is used as a measure of the performance of the system. The sigma metric measures the ratio of the quality specification to the test system imprecision. For example, the sigma metric may be used to denote the portion of tested samples that have an error less than the specified total allowable error ($TE_a$). In an embodiment of the invention where the test system imprecision is characterized by a standard deviation $\sigma$, the sigma metric is the ratio of the specified total allowable error to $\sigma$:

$$\sigma_M = \frac{TEa}{\sigma}$$

This may in turn be used to determine the probability that samples are acceptable or unacceptable. See Westgard J O. Six Sigma Quality Design & Control. Madison, Wis.: Westgard QC, Inc., 2001.

III. Overview of the Optimization Process

Figure 3:
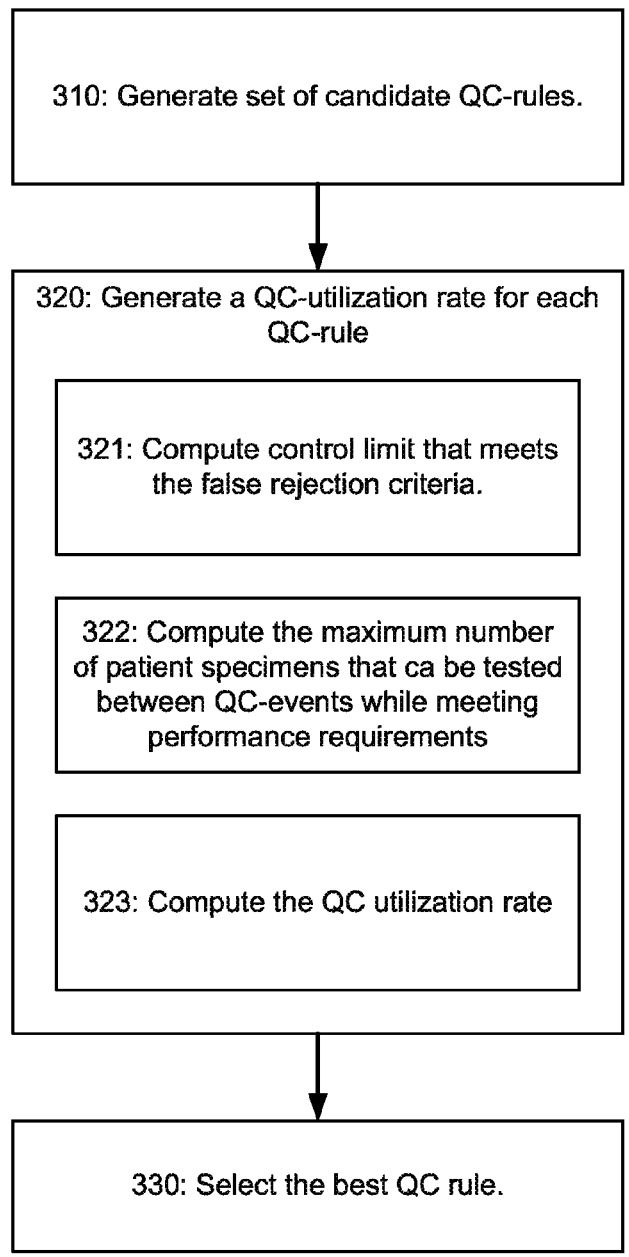
FIG. 3 is a high level flow-chart illustrating a method for optimizing a QC-strategy in accordance with an embodiment of the invention.

FIG. 3 shows a flow chart that outlines the steps of the optimization process in an embodiment of the invention. The optimization process may begin by generating a number of candidate QC rules (310). Once a set of candidate rules is generated, the quality control utilization rate may calculated for each QC rule (320), and the rule with the lowest utilization rate selected (330).

Calculating the QC utilization rate (320) for a particular QC rule may in an embodiment of the invention be broken down into three steps:

(1) Computing a control limit that meets the false rejection criteria (321);

(2) determining the number of samples that can be tested between each QC event while meeting the performance requirements (322); and (3) computing the QC utilization rate based on the number of samples tested at each QC event and the number of samples tested between each QC event (323).

Each of these steps is described in detail below.

IV. Quality Control Rules

In an embodiment of the invention, the optimal QC rule includes testing three different reference samples twice at each QC event. Furthermore, it required that the QC event shall be deemed to have failed if the chi-squared test-statistic for the reference sample test results exceeds a predetermined number (a control limit).

For example, if the three different reference samples have a reference result of 100 mg/dL, 150 mg/dL and 200 mg/dL with measurement standard deviations (SD) of 3 mg/dL, 3.5 mg/dL, and 4 mg/dL respectively, the test results may be as shown in FIG. 8.

The chi-squared test-statistic may then be generated by, for each test calculating the difference between the reference value and the expected value and dividing it by the standard deviation of the reference value and then calculating the sum of squares of these values as expressed in the following mathematical formula and the table shown in FIG. 9:

$$\chi^2 = \sum_{i=1}^{n} \left(\frac{O_i - E_i}{\sigma_i}\right)^2$$

As can be seen from the tables above, in this example, the chi-squared test-statistic is 7.548. If the control limit is 16.8, a QC event with the results shown above would be deemed to have passed.

When the chi-square test is used, the rule described above may be expressed in the following manner: chi-square(L1, L1, L2, L2, L3, L3) where L1 indicates one reference sample, L2 a different one, and L3 yet a different one. Each of these are listed twice because each is tested twice as part of a QC event. This notation is purely for informational purposes and has no impact on the performance of the invention.

Another possible QC rule may only use one or two different reference samples. Furthermore it may test each sample only once or thrice. A threshold test-statistic may be calculated for each of these tests in the same way. A rule requiring testing of a single sample once may be expressed as chi-square(L1) and a rule requiring the testing of two samples once may be expressed as chi-square(L1, L2).

The number of different reference samples available may depend on the quality control products available in the market place. For example there may only be two different reference samples available for a particular test. In such a case an embodiment of the invention may use the following candidate rules:

chi-square(L1, L2)

chi-square(L1, L1, L2, L2)

chi-square(L1, L1, L1, L2, L2, L2)

chi-square(L1)

chi-square(L1, L1)

chi-square(L1, L1, L1)

The invention does not require the use of a chi-square test for rejecting test results. In an embodiment of the invention a QC event is deemed to fail if one or more of the test results differ from the reference value by more than three standard deviations. In yet another embodiment of the invention a QC event is deemed to fail if two or more test results deviate from the reference value by more than two standard deviations in the same direction. The invention may be used with other tests, including but not limited to: cumulative sum control chart (CUSUM), exponentially weighted moving average (EWMA) and Westgard Multirules. There are a number of other ways of defining QC rules, and the invention is not limited to the ones described in this application.

V. Computing a Control Limit that Meets the False Rejection Criteria

In an embodiment of the invention where the chi-squared test is used to determine whether a QC event has been passed, a control limit is computed for each candidate rule based on a rejection criteria. This control limit may be used to determine whether a QC event is deemed a pass or a fail. For example if the relevant chi-squared test-statistic is below the control limit the QC event is deemed a pass, and otherwise it is deemed a failure.

Using the chi-squared cumulative distribution function (CDF), the observed value of the test-statistic and the degrees of freedom it is possible to determine the probability of obtaining a chi-squared test-statistic greater than the observed value when no systematic error condition is present. For the test statistic value computed above, 7.548, the corresponding number of degrees of freedom is six. Using the chi-squared CDF will reveal that there is a 27.3% chance of obtaining a chi-squared test-statistic of 7.548 or greater when no systematic error condition is present. If the computed value had been 16.8, the probability of obtaining a chi-squared test-statistic of 16.8 or greater when no systematic error condition is present would be 1%.

Using the inverse of the chi-squared cumulative distribution function (CDF) it is possible to determine a control limit for a particular false rejection criteria without having to use the chi-squared CDF for every test. The inverse of the chi-squared CDF is available in the MatLab software from MathWorks as the function chi2inv(1−$P_{fr}$, V). To obtain a control limit, this function is called with the false rejection criteria ($P_{fr}$) and the number of degrees of freedom (V), where the number of degrees of freedom is the number of reference samples tested at each QC event. Using this function with a target false rejection criteria of 1% ($P_{fr}$=0.01) and six degrees of freedom, for example a test denoted chi-square(L1, L1, L2, L2, L3, L3), the threshold test-statistic becomes 16.8. For a test denoted chi-square(L1, L1, L2, L2) with a false rejection criteria of 1% the control limit becomes 13.3.

In an embodiment of the invention where a rule that does not use the chi-squared test is employed, the control limit may be calculated by using the inverse of a CDF for a probability distribution corresponding to that test statistic, or by computer simulation in cases where the inverse of a CDF is not easily obtained.

VI. Computing the Quality Control Utilization Rate

In an embodiment of the invention computing the QC utilization rate is done as a two step process:

1. determining the number of patient samples that can be tested between QC events while meeting the performance goals; and
2. computing a ratio of the number of reference-samples tested at each QC event to the number of patient-samples tested between QC events.

As described above, there may be two separate performance criteria to be met: the maximum number of final errors (the final-max) and the number of correctable errors (correctable-max). Both of these performance criteria may be met by adjusting the number of samples tested between QC events. In other words, there are two performance requirements that must be fulfilled by adjusting one variable, the number of tests between QC events (the QC-interval). If a particular QC-interval size is determined to meet the final-max requirement, it follows that all smaller QC-interval sizes also meet this requirement. Similarly, if a particular QC interval size is determined to meet the correctable-max requirement, it follows that all smaller intervals will meet this requirement. It will also follow that if a particular QC-interval is the smallest QC-interval that meets the final-max requirement, no larger QC-intervals will meet this requirement; the same applies to the correctable-max requirement.

For this reason, the largest QC-interval that meets both the correctable-max requirement and the final-max requirement can be determined by selecting the smaller of:
1. the largest QC-interval that meets the correctable-max requirement; and
2. the largest QC-interval that meets the final-max requirement.

A. Calculating the Largest QC-Interval (Correctable Max) that Meets the Predetermined Threshold for Correctable Results Requirement In an embodiment of the invention the largest QC-interval (correctable max) that meets the predetermined threshold for correctable results requirement is determined by selecting a QC-interval such that the expected number of final errors is equal to the final-max requirement. While this may not ensure that the number of final errors never exceeds the requirement it may ensure that the requirement is met on average over a long period of time.

The statistically expected number of correctable errors may be calculated by integrating the product of the expected number of correctable errors for a systematic error of a particular size (NumCErr(SE)) and the likelihood of systematic errors that are of that particular size f(SE):

$$M_{UC} = \int_{-\infty}^{\infty} NumCErr(SE) f(SE) dSE$$

The likelihood of errors that are of a particular size (SE) may be expressed as a probability distribution function with respect to SE: f(SE). In an embodiment of the invention, a normal distribution with a mean error value of zero and a standard deviation (σ) based on the overall stability of the system may be used for f(SE).

In an embodiment of the invention the standard deviation is based on the sigma metric of the system ($\sigma_m$) and a system stability factor ($P_F$)). These may be combined by dividing the sigma metric by an inverse standard CDF of the stability factor as shown in the following expression:

$$\sigma = \frac{\sigma_m}{-invnorm\left(\frac{P_F}{2}\right)}$$

The function invnorm denotes the inverse of the standard distribution CDF, which is a normal distribution with a mean value of 0 and a standard deviation of 1. This function is implemented in the MatLab software package from MathWorks under the same function name. For a stable system, a stability factor of 0.1 may be used. For an unstable system, a stability factor or 0.5 may be used.

In an embodiment of the invention, the expected number of correctable errors may be calculated by calculating the product of:
1. the average number of patient samples tested between QC events—$N_B$;
2. the probability of an incorrect test result due to a systematic error of a particular size (SE)—$P_E$(SE).
3. the expected fraction of the patient results affected by a systematic error of a particular size in the QC interval just prior to a QC event failure—$ARL_C$(SE).

This product may be expressed using the following formula:

$$NumCErr(SE) = N_B \times P_E(SE) \times ARL_C(SE)$$

In an embodiment of the invention the probability of an incorrect test result, due to a systematic error of a particular size, $P_E$(SE), may be computed by subtracting the probability of an unacceptable patient result when the systematic error is 0 from the probability of an unacceptable patient result when the system is operating with a systematic error of SE:

$$P_E(SE) = [1-(normcdf(\sigma_m, SE, 1) - normcdf(-\sigma_m, SE, 1)] - [1-(normcdf(\sigma_m, 0, 1) - normcdf(-\sigma_m, 0, 1))]$$

Figure 2:
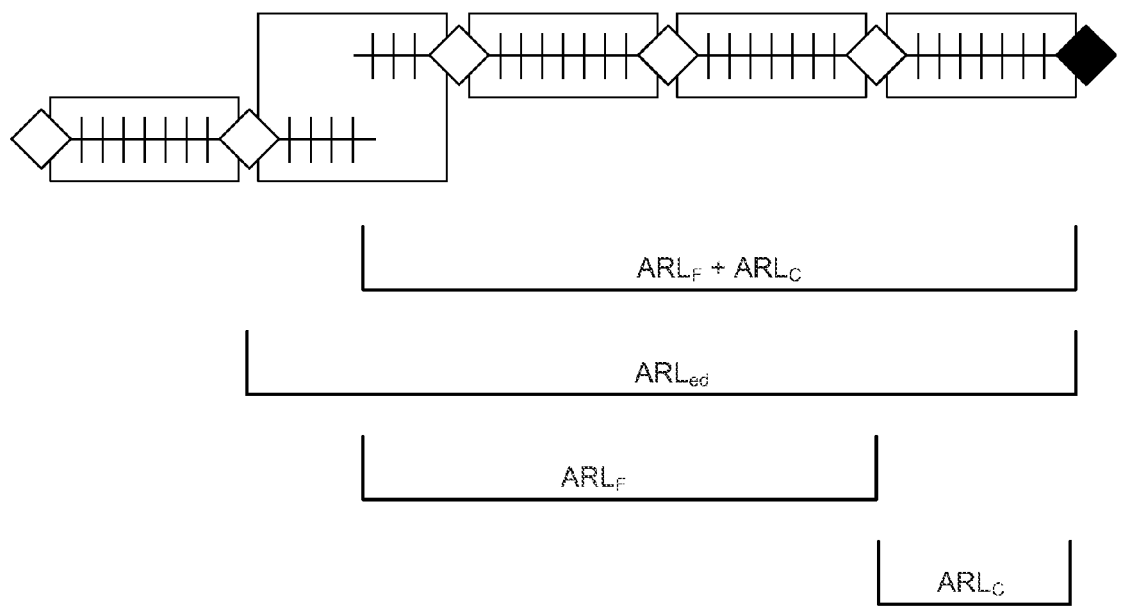
FIG. 2 shows a scenario of diagnostic testing which includes five QC-intervals and five QC-events. A systematic error occurred during the second QC-interval, and the first QC-failure occurred at the end of the fifth QC-interval. The diagram shows the various portions of the QC-intervals that are used when calculating average run-lengths for statistical purposes.

The portion of the average number of QC intervals that pass before ac QC event fails following an out of control error condition of the particular size during which errors are correctable, may also be described as the average run-length (ARL) for correctable errors. FIG. 2 illustrates what QC-intervals are used to determine the following average run-lengths:
1. The average run-length, $ARL_{ed}$(SE) denotes the number of QC-intervals that contain an out of control error condition, including the first QC-failure.
2. The average run-length for correctable errors, $ARL_C$(SE), denotes the portion of $ARL_{ed}$(SE) during which patient results with correctable errors were reported.
3. The average run-length for final errors, $ARL_F$(SE), denotes the portion of $ARL_{ed}$(SE) during which patient results with final errors were reported.

In an embodiment of the invention where the test used is a test that does not consider history such as the chi-squared test $ARL_C$(SE)+$ARL_F$(SE)=$ARL_{ed}$(SE)−½. Because not all patient results in the first QC-interval that contains the out of control error condition are unacceptable ½ is subtracted.

In an embodiment of the invention where a systematic error can begin at any patient sample with equal probability and only the patient samples that were tested in the QC-interval immediately preceding the failed QC event are retested, the ARL for correctable errors can be described with the following formula:

$$ARL_C(SE) = 1(1 - P_1(SE)) + \frac{1}{2} P_1(SE) = 1 - \frac{P_1(SE)}{2}$$

The notation $P_1$(SE) denotes the probability of a QC failure at the QC event immediately following the occurrence of the systematic error.

In an embodiment of the invention, the probability of QC-failure at the first QC-event following an unacceptable patient result, $P_1$(SE), for the chi-squared test statistic with $N_{QC}$ reference samples tested at each QC event may be calculated by using a non-central chi-squared CDF. Using a non-centrality parameter based on SE, and a threshold value based on the probability of false rejection, $P_{fr}$(SE), the following expression may be used for $P_1$(SE):

$$ncx2cdf(chi2inv(1-P_{fr}(SE), N_{QC}), N_{QC}, N_{QC} \times SE^2)$$

Inserting the function for the number of correctable errors into the integral from above, the following formula shows the expected number of correctable errors:

$$M_{UC} = \int_{-\infty}^{\infty} N_B \times P_E(SE) \times ARL_C(SE) f(SE) dSE$$

Since the number of samples between QC events in the expression above does not depend on SE this formula can be rearranged in the following manner to get a formula that can be used to calculate the largest QC-interval that meets the correctable-max requirement:

$$N_{BC} = \frac{M_{UC}}{\int_{-\infty}^{\infty} P_E(SE) \times ARL_C(SE) f(SE) dSE}$$

where $N_{BC}$ denotes the value for $N_B$ that meets the $M_{UC}$ criteria.

In an embodiment of the invention, the number of correctable errors is restricted by a maximum-value instead of an expected value. When a maximum is used, the integral in the expression above may be replaced with the following:

$$\max_{SE}\{P_E(SE) \times ARL_C(SE)\}$$

In an embodiment of the invention, this expression will be maximal when SE tends to infinity, in such a case $N_B$ would be determined by choosing SE which is high-enough to encompass a portion of possible systematic errors i.e. 99.9%.

In another embodiment of the invention $N_B$ may be determined by simulation.

B. Calculating the Largest QC-Interval (Final Max) that Meets the Predetermined Threshold for Final Results Requirement The largest QC interval (final max) that meets the predetermined threshold for final results requirement may be calculated in a similar way to the largest QC-interval that meets the correctable-max requirement, with $ARL_F(SE)$ substituted for $ARL_C(SE)$ in the formulas. When a systematic error can begin at any patient sample with equal probability and only the patient samples that were tested in the QC-interval immediately preceding the failed QC event are retested, $ARL_F(SE)$ can be described with the following formula:

$$ARL_F(SE) = ARL_{ed}(SE) - \tfrac{1}{2} - ARL_C(SE)$$

where $ARL_{ed}(SE)$ is the average number of QC events required to obtain a QC failure in the presence of a systematic error SE. $ARL_{ed}(SE)$ may be computed numerically or by computer simulation depending on the complexity of the quality control test statistic.

FIG. 2 illustrates the relationships among the average run-lengths. The sum of $ARL_C(SE)$ and $ARL_F(SE)$ is the total run-length from the beginning of the systematic error. If a systematic error can begin with equal probability at any patient sample, the expected total run-length is ½ less that the expected number of QC-events following the first unacceptable patient result In an embodiment of the invention, the same formula is used to calculate the largest QC-interval that meets the final-max requirement and largest QC-interval that meets the correctable-max requirement, with the only difference being that the average run-length for correctable errors ($ARL_C(SE)$) is replaced with the average run-length for final errors ($ARL_F(SE)$). The following expression may then be used to calculate the largest QC-interval that meets the final-max requirement:

$$N_{BF} = \frac{M_{UF}}{\int_{-\infty}^{\infty} P_E(SE) \times ARL_F(SE) f(SE) dSE}$$

The sum of $ARL_C(SE)$ and $ARL_F(SE)$ is the total run-length. Since the first unacceptable patient-result on average occurs half-way between QC-events, the expected total run-length is ½ less that the expected number of QC-events following the first unacceptable patient result, $ARL_{ED}(SE)$, including the first QC-failure following it:

$$ARL_{ed}(SE) = ARL_C(SE) + ARL_F(SE) + \tfrac{1}{2}$$

In an embodiment of the invention using a rule that does not use history, such as the chi-squared test, $ARL_{ed}(SE)$ may be calculated by adding the probabilities of each successive QC-event being encountered using the following formula, where $P_1(SE)$ is the probability of failure at the next QC-event following an error. For example: the probability of encountering the first QC-event is 1; the probability of encountering the second QC-event is the probability of passing the first QC-event. The probability of encountering the third QC-event is the probability of failing the first and second QC-event. $ARL_{ed}(SE)$ may therefore be calculated by adding all these probabilities to infinity:

$$\begin{aligned}ARL_{ed} &= 1 + \overline{P_1(SE)} + \overline{P_1(SE)}^2 + \overline{P_1(SE)}^3 \ldots \\ &= 1 + (1 - P_1(SE)) + (1 - P_1(SE))^2 + (1 - P_1(SE))^3 \ldots \\ &= \sum_{i=0}^{\infty} (1 - P_1(SE))^i \\ &= \frac{1}{P_1(SE)}\end{aligned}$$

Using this formula, and the observation that $ARL_{ed}(SE) = ARL_C(SE) + ARL_F(SE) + \tfrac{1}{2}$, $ARL_F(SE)$ may be determined using one of the following expressions:

$$ARL_{ed}(SE) = \frac{1}{P_1(SE)}$$

Figure 4:
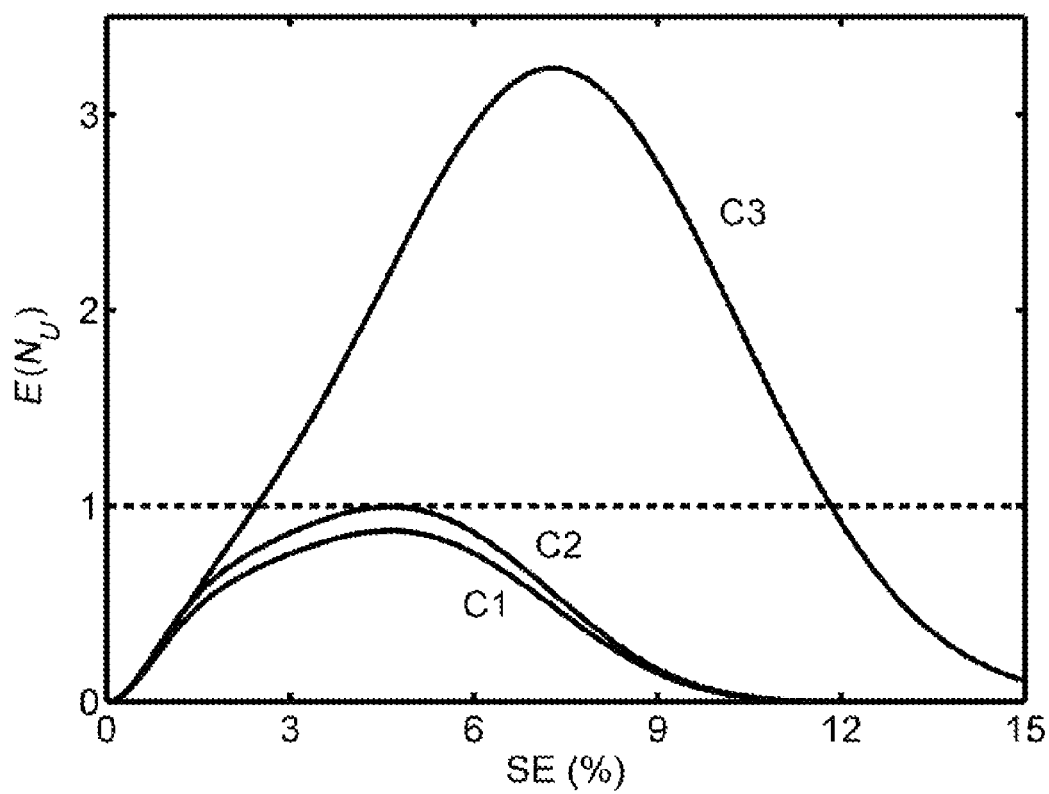

When the testing system is subject to a systematic error of a particular size (SE), the size of this error affects both the possibility of an unacceptable patient result, and the possibility of QC-failure. A small systematic error may only cause a small chance of unacceptable patient results, but will also only cause a small chance of QC-failure. Similarly, a large systematic error will cause a great chance of unacceptable patient results, but also a great chance of QC-failure. It may therefore be that once the systematic error goes above a certain value, the expected number of final-errors decreases as the systematic error grows due to the increased chance of quick QC-failure. For this reason, in an embodiment of the invention the final-maximum requirement may be applied to limit the maximum number of final errors instead of the expected number of final errors. FIG. 4 illustrates how the expected number of final errors may vary with SE for three different quality control rules.

To restrict the maximum number of final errors in this way, the expected number of final errors is calculated for a range of systematic errors (SE), ranging from very small to very large, and then the largest expected number of final errors is selected. The expected number of final errors for a particular QC-interval-size ($N_B$) and systematic error may be determined by multiplying the probability of an unacceptable patient result when the system is subject to a systematic error of size SE: $P_E(SE)$ and the average run-length for final errors:

$$N_B \times P_E(SE) \times ARL_F(SE)$$

The maximum number of final errors may therefore be expressed as:

$$\max_{SE}\{N_B \times P_E(SE) \times ARL_F(SE)\}$$

To ensure that the final-maximum requirement is met, $N_B$ must be selected such that the maximum number of final $M_{UF}$ errors equals the maximum number of final errors:

$$M_{UF} = \max_{SE}\{N_B \times P_E(SE) \times ARL_F(SE)\}$$

When the interval-size does not depend on SE the expression may be re-arranged in the following ways:

$$M_{UF} = N_B \times \max_{SE} \{P_E(SE) \times ARL_F(SE)\}$$

$$N_{BF} = \frac{M_{UF}}{\max_{SE} \{P_E(SE) \times ARL_F(SE)\}}$$

where $N_{BF}$ denotes the value for $N_B$ that meets the $M_{UF}$ criterion. Curve C2 in FIG. 4 shows the result of using this formula to determine $N_{BF}$ when $M_{UF}$ was set to 1.

C. Computing the QC Utilization Rate

Once the maximum QC-interval size for the final-maximum requirement ($N_{BF}$) and the maximum QC-interval size for the correctable-maximum requirement ($N_{BC}$) have been determined, the largest QC-interval that meets both of these requirements ($N_B$) will be the smaller of the two:

$$N_B = \min\{N_{BC}, N_{BF}\}$$

Having calculated the largest QC-interval that meets these requirements for a particular QC-rule, the QC-utilization rate can be calculated by dividing the number of QC-tests per QC-event by the number of patient-samples tested in each QC-interval:

$$R_{QC} = \frac{N_{QC}}{N_B}$$

This ratio may be calculated in a number of ways; in an embodiment of the invention the ratio may be calculated with a particular testing run in mind, including a QC-event at the start of the run, QC-events between each QC-interval and a QC-event at the end of the run. When the only aim is to rank the rules in order the method used may be of little implication. However, where more analysis on the different rules is performed, the way the ratio is calculated may be of relevance.

D. Selecting the Best QC-Rule

Having calculated a QC-utilization rate and a maximum number of samples between QC-events, the most efficient rule can be selected by choosing the rule with the lowest QC-utilization rate.

Where two rules have the same QC utilization rate, or the rates are within a certain margin of each other it may be desirable to select the rule with the lowest false rejection rate or the smallest number of reference samples tested per QC-event.

Figure 5:
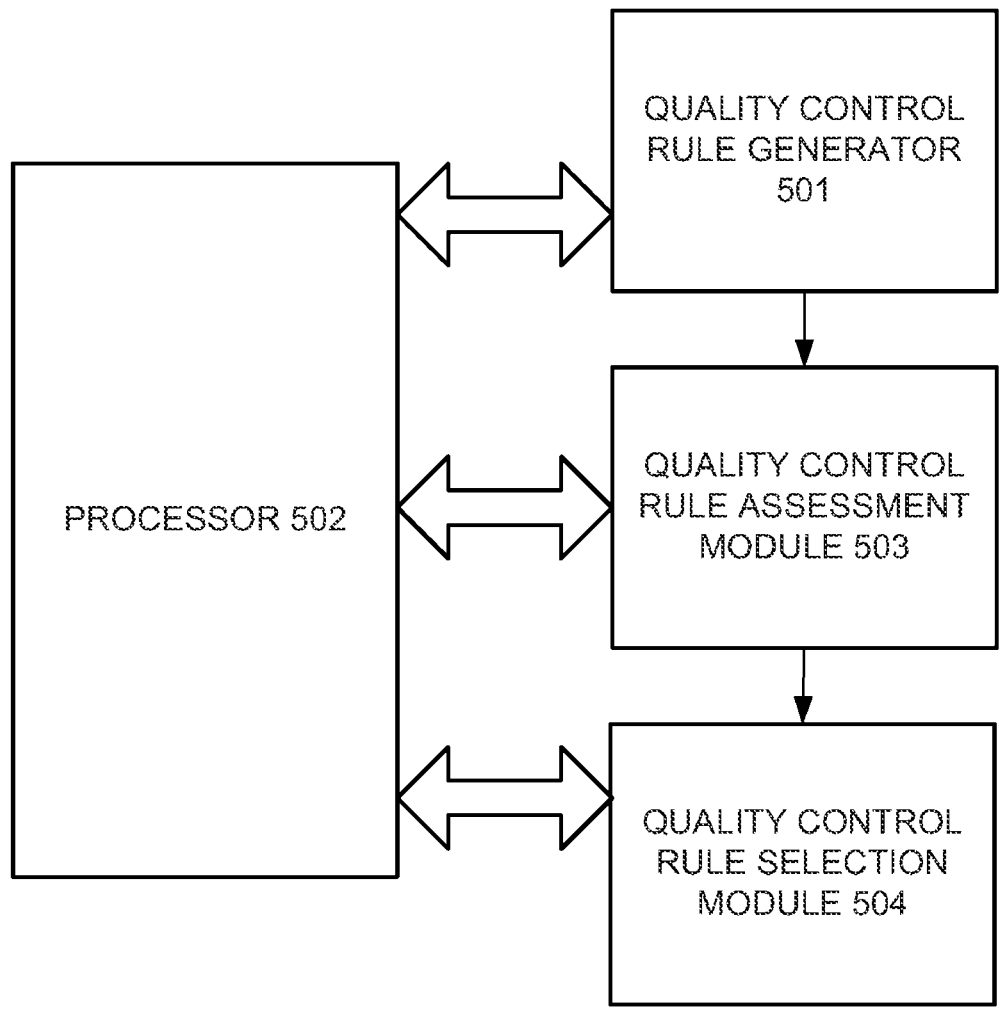
FIG. 5 is a high level block diagram illustrating a system for optimizing a quality control strategy in accordance with an example embodiment of the invention.

An example system implementing the quality control optimization process is shown in FIG. 5, which is a high level block diagram illustrating a system for optimizing a quality control strategy in accordance with an example embodiment of the invention. The diagram shows a processor (502) and its interaction with a quality control rule generator (501) that generates candidate quality control rules, a quality control rule assessment module (503) that computes a quality control unitization rate for each for each of the candidate control rules generated by the quality control rule generator and a quality control rule selection module (504) that selects the candidate quality control rule with the best quality control utilization rate. These modules and generators may be implemented in a number of ways, including as a standalone device or a physical component of an implementation, a software module, a piece of code in an overall computer program or in a number of other ways.

Figure 6:
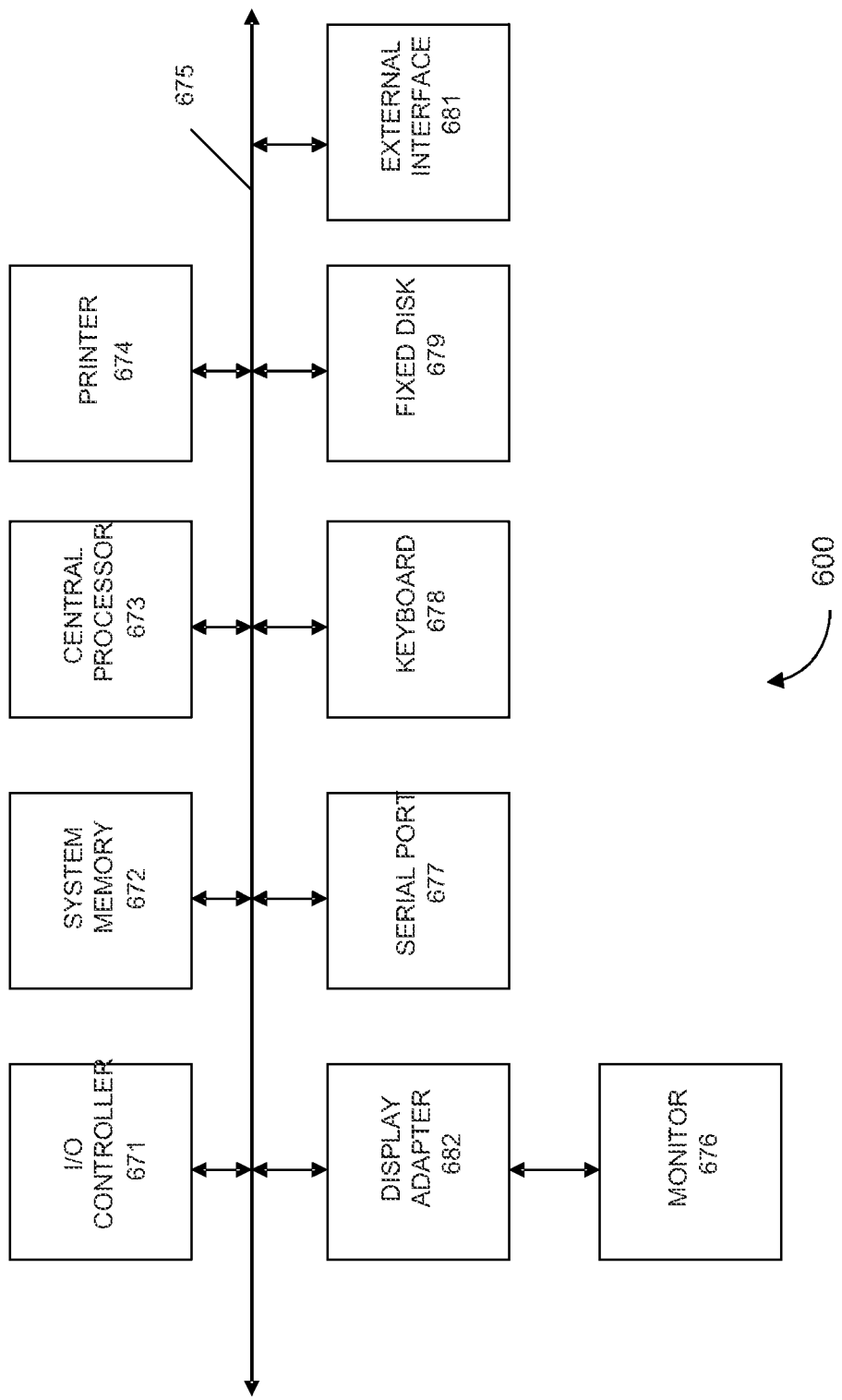
FIG. 6 shows a block diagram of an example computer system usable with system and methods according to embodiments of the present invention.

Any of the computer systems mentioned herein may utilize any suitable number of subsystems. Examples of such subsystems are shown in FIG. 6 in computer apparatus 600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 6 are interconnected via a system bus 675. Additional subsystems such as a printer 674, keyboard 678, fixed disk 679, monitor 676, which is coupled to display adapter 682, and others are shown. Peripherals and input/output (I/O) devices, which couple to I/O controller 671, can be connected to the computer system by any number of means known in the art, such as serial port 677. For example, serial port 677 or external interface 681 can be used to connect computer system 600 to a wide area network such as the Internet, a mouse input device, or a scanner. The interconnection via system bus 675 allows the central processor 673 to communicate with each subsystem and to control the execution of instructions from system memory 672 or the fixed disk 679, as well as the exchange of information between subsystems. The system memory 672 and/or the fixed disk 679 may embody a computer readable medium. Any of the values mentioned herein can be output from one component to another component and can be output to the user.

A computer system can include a plurality of the same components or subsystems, e.g., connected together by external interface 681. In some embodiments, computer systems, subsystem, or apparatuses can communicate over a network. In such instances, one computer can be considered a client and another computer a server. A client and a server can each include multiple systems, subsystems, or components, mentioned herein.

Figure 7:
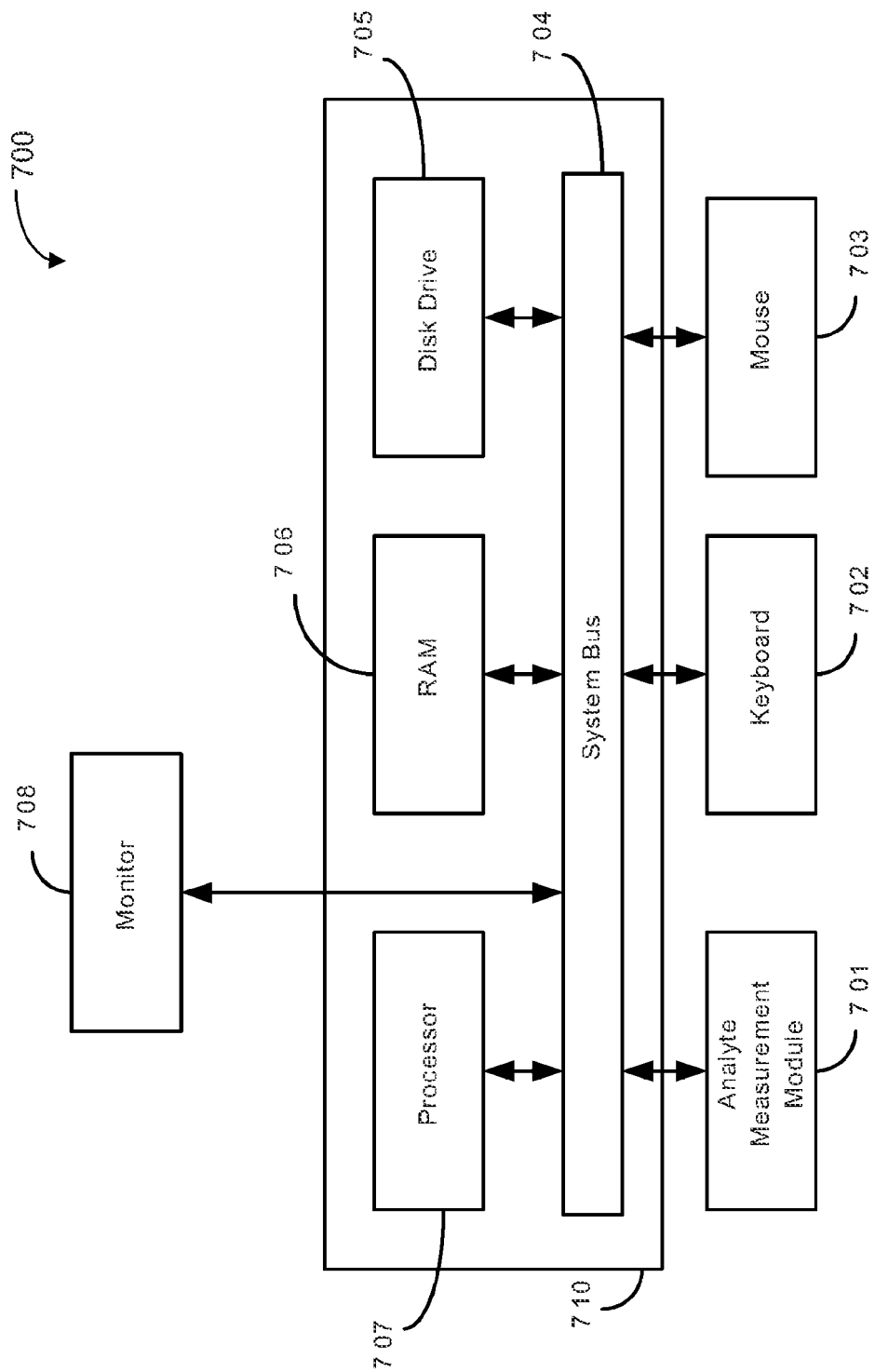
FIG. 7 is a block diagram of an apparatus for determining one or more properties of a biological sample according to embodiments of the present invention.

FIG. 7 is a block diagram of an apparatus 700 that can be used to execute any of the embodiments of the invention. Apparatus 700 include a computer system 710 and has a number of input modules. An analyte measurement module 701 is used to measure the analyte responses in a test sample. This module can vary between different embodiments of the invention depending on the measurement method selected to measure the analyte responses. Also shown are a standard keyboard 702 and mouse 703. Apparatus 700 can also contains a variety of typical computer components inside computer system. These components can include a system bus 704, one or more disk drives 705, RAM 706, and a processor 707. FIG. 7 also shows a monitor 708 that allows information to be displayed to a user of the system. Other components can also be present depending on the exact nature of the embodiment. In various embodiments, the apparatus can include any of the features of computer system 700.

In one embodiment of the invention, a sample is placed in the analyte measurement module 701 where the sample is further processed and the analyte responses in the sample are measured. This information is then transferred into the computer system along a system bus 804, and an appropriate conversion method is applied to the analyte response data using the processor 807. The instructions the processor 707 executes to implement instructions for any methods described herein, where the instruction can be stored on a computer readable medium such as the RAM 706 or disk drive 705. The results from the methods can then be displayed on the monitor 708. Alternative embodiments of the invention can output results using other communications means. For example, the computer system could print the measured ratio using a printer or send the measured ratio to another computer over a network.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method for optimizing a quality control strategy comprising:
   generating, with a processor, a set of candidate quality control rules;
   for each candidate rule:
      computing a control limit that meets a false rejection criteria;
      computing, using the control limit, a correctible maximum by calculating how many patient samples can be tested between quality control events while keeping the number of correctible results with an error exceeding a predetermined threshold below a predetermined value;
      computing, using the control limit, a final maximum by calculating how many patient samples that can be tested between quality control events while keeping the number of final results with an error exceeding a predetermined threshold below a predetermined value;
      selecting a quality control interval size, the quality control interval size being a smallest value of the correctible maximum and the final maximum; and
      computing a quality control utilization rate by dividing the number of reference samples tested at each quality control event by the quality control interval size; and
   selecting a candidate quality control rule based on the quality control utilization rates of the set of candidate quality control rules.

2. The method of claim 1 wherein at least one of the candidate quality control rules is further adapted for testing at least two reference specimens to obtain a test value for each specimen, wherein each specimen has a corresponding reference value.

3. The method of claim 2 wherein the at least one of the candidate quality control rules is further adapted for using a chi-squared test to determine whether the differences between the test values and the reference values is due to a systematic error.

4. The method of claim 2 wherein the at least one of the candidate quality control rules is further adapted for:
   computing a test statistic by calculating the sum of the square of the difference between the test value and the reference value for each reference specimen tested;
   determining a probability that the differences between the test values and the reference values are caused by a systematic error by comparing the test-statistic to a chi-squared distribution; and
   determining whether the quality control rule was passed by determining whether the probability that the differences between the test values and the reference values are caused by a systematic error is above a threshold value.

5. The method of claim 4 wherein computing a control limit that meets a false rejection criteria comprises using the inverse of the chi-squared cumulative probability distribution function to determine a threshold test-statistic value based on the false rejection criteria and the number of reference specimens to be tested.

6. The method of claim 1 wherein computing, using the control limit, a correctible maximum further comprises:
   selecting a number of patient specimens that can be tested between quality control events such that an expected number of correctible results equals the predetermined threshold for correctible results.

7. The method of claim 6 wherein the expected number of correctible results is equal to an integral over the acceptable margin of error from negative infinity to infinity of the product of:
   the number of patient specimens that can be tested between quality control events;
   a probability of obtaining an unacceptable patient result;
   an expected portion of the samples tested after a last passed quality control event that are unacceptable; and
   a frequency distribution for the magnitude of errors for unacceptable patient results.

8. The method of claim 7 wherein the expected portion of the samples tested after a last passed quality control event that have an error exceeding the predetermined threshold is computed by subtracting one half of the probability of obtaining a patient result with an error exceeding the predetermine threshold from one.

9. The method of claim 7 wherein the frequency distribution for the magnitude of errors for unacceptable patient results is a normal distribution.

10. The method of claim 1 wherein selecting a candidate rule based on a predetermined criterion comprises selecting the candidate rule having the lowest quality control utilization rate.

11. A method for optimizing a quality control strategy comprising:
    generating, with a processor, a set of candidate quality control rules, wherein each rule is adapted for testing at least one reference sample having a reference value to obtain a test value, and computing a chi-squared test statistic based on the test value and reference value for each reference sample tested and determining whether the test statistic is greater than a control limit;
    for each candidate rule, using the processor:
        computing a control limit that meets a false rejection criteria using the inverse of the chi-squared cumulative probability distribution function;
        computing, using the control limit, a correctible maximum by calculating how many patient samples that can be tested between quality control events while keeping the number of correctible results with an error exceeding a predetermined threshold below a predetermined value;
        computing, using the control limit, a final maximum by calculating how many patient samples that can be tested between quality control events while keeping the number of final results with an error exceeding a predetermined threshold below a predetermined value;
        selecting as a quality control interval size, a smallest value of the correctible maximum and the final maximum; and
        computing a quality control utilization rate by dividing the number of reference samples tested at each quality control event by the quality control interval size; and
    selecting the candidate.

12. A system for optimizing a quality control strategy comprising:
    a processor;
    a quality control rule generator operable to generate a set of candidate quality control rules;
    a quality control rule assessment module operable to, using the processor, compute a maximum number of patient specimens that can be tested between quality control events while keeping the expected number of correctible unacceptable results below a predetermined threshold for correctible results and keeping the expected number of final unacceptable results below a predetermined threshold for final unacceptable results for a candidate quality control rule; and
    a quality control rule section module operable to, using the processor: select a candidate rule for which a best quality control utilization rate was computed.

13. The system of claim 12 wherein at least one of the candidate quality control rules is further adapted for testing at least two reference specimens to obtain a test value for each specimen, wherein each specimen has a corresponding reference value.

14. The system of claim 13 wherein the at least one of the candidate quality control rules is further adapted for using a chi-squared test to determine whether the differences between the test values and the reference-values is due to a systematic error.

15. The system of claim 13 wherein the at least one of the candidate quality control rules is further adapted for:
    computing a test statistic by calculating the sum of the square of the difference between the test-value and the reference-value for each reference specimen tested;
    determining a probability that the differences between the test-values and the reference-values are caused by a systematic error by comparing the test-statistic to a chi-squared distribution; and
    determining whether the quality control rule was passed by determining whether the probability that the differences between the test-values and the reference-values are caused by a systematic error is above a threshold value.

16. The system of claim 12 wherein the quality control rule assessment module is further operable to:
    select a number of patient specimens that can be tested between quality control events such that an expected number of correctible results equals the predetermined threshold for correctible results.

17. The system of claim 16 wherein the expected number of correctible results is equal to an integral over the acceptable margin of error from negative infinity to infinity of the product of:
    the number of patient specimens that can be tested between quality control events;
    a probability of obtaining an unacceptable patient result;
    an expected portion of the samples tested after a last passed quality control event that are unacceptable; and
    a frequency distribution for the magnitude of errors for unacceptable patient results.

18. The system of claim 13 wherein selecting a candidate rule based on a predetermined criterion comprises selecting the candidate rule having the lowest quality control utilization rate.

19. A computer program product comprising a non-transitory computer-readable storage medium storing a plurality of computer-readable instructions tangibly, which, when executed by a computing system, provide a method for optimizing a quality control strategy comprising, the plurality of instructions comprising:
    generating a set of candidate quality control rules;
    for each candidate quality control rule:
        computing a control limit that meets a false rejection criteria;
        computing a maximum number of patient specimens that can be tested between quality control events while keeping the expected number of correctible unacceptable results below a predetermined correctible maximum and keeping the expected number of final unacceptable results below a predetermined final maximum; and
        computing a quality control utilization rate; and
    selecting a candidate quality control rule based on the quality control utilization rates of the set of candidate quality control rules.

20. The computer program product of claim 19 wherein at least one of the candidate quality control rules is further adapted for testing at least two reference specimens to obtain a test value for each specimen, wherein each specimen has a corresponding reference value.

21. The computer program product of claim 20 wherein the at least one of the candidate quality control rules is further adapted for using a chi-squared test to determine whether the differences between the test values and the reference-values is due to a systematic error.

22. The computer program product of claim 20 wherein the at least one of the candidate quality control rules is further adapted for:
   computing a test statistic by calculating the sum of the square of the difference between the test-value and the reference-value for each reference specimen tested;
   determining a probability that the differences between the test-values and the reference-values are caused by a systematic error by comparing the test-statistic to a chi-squared distribution; and
   determining whether the quality control rule was passed by determining whether the probability that the differences between the test-values and the reference-values are caused by a systematic error is above a threshold value.

23. The computer program product of claim 22 wherein computing a control limit that meets a false rejection criteria comprises using the inverse of the chi-squared cumulative probability distribution function to determine a threshold test-statistic value based on the false rejection criteria and the number of reference-specimens to be tested.

24. The computer program product of claim 19 wherein computing, using the control limit, a correctible maximum further comprises:
   selecting a number of patient specimens that can be tested between quality control events such that an expected number of correctible results equals the predetermined threshold for correctible results.

25. The computer program product of claim 24 wherein the expected number of correctible results is equal to an integral over the acceptable margin of error from negative infinity to infinity of the product of:
   the number of patient specimens that can be tested between quality control events;
   a probability of obtaining an unacceptable patient result;
   an expected portion of the samples tested after a last passed quality control event that are unacceptable; and
   a frequency distribution for the magnitude of errors for unacceptable patient results.

26. The computer program product of claim 20 wherein selecting a candidate rule based on a predetermined criterion comprises selecting the candidate rule having the lowest quality control utilization rate.

* * * * *